(12) United States Patent
Panabières et al.

(10) Patent No.: US 8,524,493 B2
(45) Date of Patent: Sep. 3, 2013

(54) RELEASED CYTOKERATINS AS MARKERS FOR EPITHELIAL CELLS

(75) Inventors: Catherine Panabières, Clapiers (FR); Klaus Pantel, Hamburg (DE); Jean-Pierre Vendrell, Castelnau-le-lez (FR)

(73) Assignee: Centre Hospitalier Universitaire de Montpellier, Montpellier (FR)

( * ) Notice: Subject to any disclaimer, the term of this patent is extended or adjusted under 35 U.S.C. 154(b) by 852 days.

(21) Appl. No.: 12/439,744

(22) PCT Filed: Sep. 4, 2007

(86) PCT No.: PCT/IB2007/002549
§ 371 (c)(1),
(2), (4) Date: Mar. 3, 2010

(87) PCT Pub. No.: WO2008/029251
PCT Pub. Date: Mar. 13, 2008

(65) Prior Publication Data
US 2010/0184083 A1 Jul. 22, 2010

Related U.S. Application Data

(60) Provisional application No. 60/842,902, filed on Sep. 7, 2006.

(51) Int. Cl.
*C12N 5/00* (2006.01)
(52) U.S. Cl.
USPC ............ 435/374; 435/2; 435/6; 435/7.1; 435/287.2; 435/371; 435/373; 435/383; 436/63; 436/64; 436/173; 436/177; 530/326; 530/327; 530/328; 530/344; 530/357

(58) Field of Classification Search
USPC ............ 435/2, 6, 7.1, 7.23, 7.94, 371, 372.1, 435/373, 374, 383, 287.2; 436/548, 56, 63, 436/64, 173, 177; 530/300, 326–328, 344, 530/357
See application file for complete search history.

(56) References Cited

U.S. PATENT DOCUMENTS

| 4,775,620 A | 10/1988 | Cardiff et al. |
| 5,288,614 A * | 2/1994 | Bodenmuller et al. ...... 435/7.23 |
| 2002/0012931 A1 | 1/2002 | Waldman et al. |
| 2005/0079557 A1 | 4/2005 | Vendrell et al. |

FOREIGN PATENT DOCUMENTS
WO WO 2004/024957 A2 3/2004

OTHER PUBLICATIONS

Racila et al. (Detection and characterization of carcinoma cells in the blood, Proc. Natl. Acad. Sci. 95: 4589-4594 (Apr. 1998).*

(Continued)

*Primary Examiner* — Gail R Gabel
(74) *Attorney, Agent, or Firm* — Brinks Hofer Gilson & Lione

(57) ABSTRACT

The present invention is directed to methods of detecting viable epithelial cells in a sample. The method includes isolating the sample comprising cells from a patient and culturing the cells for a time sufficient for an epithelial cell-specific marker to be released from the cells. The marker includes a substantially full-length cytokeratin. The method further includes detecting the released marker. Detection of the marker indicates the presence of disseminated epithelial cells. Methods are also directed to identifying disseminated epithelial tumor cells.

20 Claims, 3 Drawing Sheets

(56) References Cited

OTHER PUBLICATIONS

Ding et al. From Proteomic Analysis to Clinical Significance—Overexpression of cytokeratin 19 correlates with hepatocellular carcinoma metastasis, Molecular & Cellular Proteomics 3: 73-81 (2004).*
Matouskova et al. Temporal in vitro expansion of the luminal lineage of human mammary epithelial cells achieved with the 3T3 feeder layer technique. Breast Cancer Research and Treatment 60: 241-249 (2000).*
Barak et al. Clinical utility of cytokeratins as tumor marker, Clinical Biochemistry 37: 529-540 (2004).*
Alix-Panabieres, C., Brouillet, J.P., Fabbro, M., Yssel, H., Rousset, T., Maudelonde, T., Choquet-Kastylevsky, G., and Vendrell, J.P. 2005. Characterization and enumeration of cells secreting tumor markers in the peripheral blood of breast cancer patients. J Immunol Methods 299:177-188.
Alix-Panabieres, C., Rebillard, X., Brouillet, J.P., Barbotte, E., Iborra, F., Segui, B., Maudelonde, T., Jolivet-Reynaud, C., and Vendrell, J.P. 2005. Detection of circulating prostate-specific antigen-secreting cells in prostate cancer patients. Clin Chem 51:1538-1541.
Alix-Panabieres, C. et al.; "Detection and Characterization of Putative Metastatic Precursor Cells in Cancer Patients;" Clinical Chemistry 53, No. 3, 2007; pp. 537-539.
Alix-Panabieres, C. et al; "Detection and Characterization of Putative Metastatic Precursor Cells in Cancer Patients;" Poster presented at The 4th International Meeting on Cancer Molecular Markers in Stone Mountain, Georgia, U.S.A., Sep. 8-10, 2006.
Allard, W.J., Matera, J., Miller, M.C., Repollet, M., Connelly, M.C., Rao, C., Tibbe, A.G.J., Uhr, J.W., and Terstappen, L.W. 2004. Tumor cells circulate in the peripheral blood of all major carcinomas but not in healthy subject or patients with nonmalignant diseases. Clin Cancer Res 10:6897-6904.
Balducci, E., Azzarello, G., Valori, L., Toffolatti, L., Bolgan, L., Valenti, M.T., Bari, M., Pappagallo, G.L., Ausoni, S., and Vinante, O. 2005. A new nested primer pair improves the specificity of CK-19 mRNA detection by RT-PCR in occult breast cancer cells. Int J Biol Markers 20:28-33.
Barak, V., Goike, H., Panaretakis, K.W., and Einarsson, R. 2004. Clinical utility of cytokeratins as tumor markers. Clin Biochem 37:529-540.
Berois, N. et al.; "Detection of Rare Breast Cancer Cells. Comparison of an Immunomagnetic Separation Method with Immunocytochemistry and RT-PCR;" Anticancer Research 17. 2639-2646 (1997); XP002900516.
Bodenmuller, H., Ofenloch-Hahnle, B., Lane, E.B., Dessauer, A., Bottger, V., and Donie, F. 1994. Lung cancer-associated keratin 19 fragments: development and biochemical characterisation of the new serum assay Enzymun-Test CYFRA 21-1. Int J Biol Markers 9:75-81.
Braun, S., Pantel, K., Muller, P., Janni, W., Hepp, F., Kentenich, C.R., Gastroph, S., Wischnik, A., Dimpfl, T., Kindermann, G., et al. 2000. Cytokeratin-positive cells in the bone marrow and survival of patients with stage I, II, or III breast cancer. N. Engl J Med 342:525-533.
Chu et al.; Histopathology, 2002, 40:403-39.
Cordoba, F., Lavabre-Bertrand, T., Salhi, S.L., Huguet, M.F., Gerfaux, J., Rossi, J.F., and Vendrell, J.P. 2000. Spontaneous monoclonal immunoglobulin-secreting peripheral blood mononuclear cells as a marker of disease severity in multiple myeloma. Br J Haematol 108:549-558.
Coulombe, "'Hard' and 'soft' principles defining the structure, function and regulation of keratin intermediate filaments"; Curr Opin Cell Biol, 2002, 14: 110-122.
Coulombe, PA; Curr Opin Cell Biol 5:17-29; 1993.
Cristofanilli, M., Budd, G.T., Ellis, M.J., Stopeck, A., Matera, J., Miller, M.C., Reuben, J.M., Doyle, G.V., Allard, W.J., Terstappen, L.W., et al. 2004. Circulating tumor cells, disease progression, and survival in metastatic breast cancer. N. Engl J Med 351:781-791.
Czerkinsky, C., Nilsson, L.A., Nygren, H., Ouchterlony, O., and Tarkowski, A. 1983. A solid-phase enzyme-linked immunospot (ELISPOT) assay for enumeration of specific antibody-secreting cells. J Immunol Methods 65:109-121.
Ding et al.; Mol Cell Proteomics 3:73-81; 2004.
Dohmoto, K., Hojo, S., Fujita, J., Yang, Y., Ueda, Y., Bandoh, S., Yamaji, Y., Ohtsuki, Y., Dobashi, N., Ishida, T., et al. 2001. The role of caspase 3 in producing cytokeratin 19 fragment (CYFRA21-1) in human lung cancer cell lines. Int J Cancer 91:468-473.
Fuchs, Ann Rev Biochem 1994 63:345-82.
Gudjonsson, T. et al.; "Isolation, immoralization, and characterization of a human breast epithelial cell line with stem cell properties;" Genes & Development 16:693-706; 2002; XP-002241566.
Janni, W., Rack, B., Schindlbeck, C., Strobl, B., Rjosk, D., Braun, S., Sommer, H., Pantel, K., Gerber, B., and Friese, K. 2005. The persistence of isolated tumor cells in bone marrow from patients with breast carcinoma predicts an increased risk for recurrence. Cancer 103:884-891.
Ku, N. O., Liao, J., and Omary, M.B. 1997. Apoptosis generates stable fragments of human type I keratins. J Biol Chem 272:33197-33203.
Ku, N. O., "Effect of Mutation and Phosphorylation of Type I Keratins on Their Caspase-mediated Degradation"; J Biol Chem, vol. 276, No. 29, Jul. 20, 2001; pp. 26792-26798.
Leers, M.P. et al.; J Pathol 187:567-572; 1999.
Matoušková et al.; "Temporal in vitro expansion of the luminal lineage of human mammary epithelial cells achieved with the 3T3 feeder layer technique;" Breast Cancer Research and Treatment 60: 241-249, 2000; XP-002469081.
Meng, S., Tripathy, D., Frenkel, E.P., Shete, S., Naftalis, E.Z., Huth, J.F., Beitsch, P.D., Leitch, M., Hoover, S., Euhus, D., et al. 2004. Circulating tumor cells in patients with breast cancer dormancy. Clin Cancer Res 10:8152-8162.
Moll, R., Franke, W.W., Schiller, D.L., Geiger, B., and Krepler, R. 1982. The catalog of human cytokeratins: patterns of expression in normal epithelia, tumors and cultured cells. Cell 31:11-24.
Nisman, Cancer, 1998, 10: 1850-1859.
Pantel, K. et al.; Nat Rev Cancer 4:448-56; 2004.
Pantel, K., Felber, E., and Schlimok, G. 1994. Detection and characterization of residual disease in breast cancer. J Hematother 3:315-322.
Petersen, O.W. et al.; "Epithelial progenitor cell lines as models of normal breast morphogenesis and neoplasia;" Cell Prolif. 2003, 36 (Suppl. 1). 33-44; XP-002469082.
Petitjean, G. et al.; J Clin Virol 39:1-8; 2007.
Pujol et al.; Cancer Res 53:61-6; 1993.
Racila, E., Euhus, D., Weiss, A.J., Rao, C., McConnell, J., Terstappen, L.W., and Uhr, J.W. 1998. Detection and characterization of carcinoma cells in the blood. Proc Natl Acad Sci U S A 95:4589-4594.
Rappsilber, J. et al.; Anal Chem 75:663-670; 2003.
Ring, A.E., Zabaglo, L., Ormerod, M.G., Smith, I.E., and Dowsett, M. 2005. Detection of circulating epithelial cells in the blood of patients with breast cancer: comparison of three techniques. Br J Cancer 92:906-912.
Rrydlander, Eur J Biochem, 1996, 241:309-14.
Schoenfeld, A., Kruger, K.H., Gomm, J., Sinnett, H.D., Gazet, J.C., Sacks, N., Bender, H.G., Luqmani, Y., and Coombes, R.C. 1997. The detection of micrometastases in the peripheral blood and bone marrow of patients with breast cancer using immunohistochemistry and reverse transcriptase polymerase chain reaction for keratin 19. Eur J Cancer 33:854-861.
Sheard, M.A., Vojtesek, B., Simickova, M., and Valik, D. 2002. Release of cytokeratin-18 and -19 fragments (TPS and CYFRA 21-1) into the extracellular space during apoptosis. J Cell Biochem 85:670-677.
Smerage, J.B., and Hayes, D.F. 2006. The measurement and therapeutic implications of circulating tumour cells in breast cancer. Br J Cancer 94:8-12.
Steinert, Ann Rev Biochem, 1988, 57:593-625.
Vendrell, J.P. 2004. Peripheral blood naïve and memory B cells. In Measuring immunity : basic biology and clinical assessment. E.A. Press, editor. London. 277-289.

Willipinski-Stapelfeldt, B., Riethdorf, S., Assmann, V., Woelfle, U., Rau, T., Sauter, G., Heukeshoven, J., and Pantel, K. 2005. Changes in cytoskeletal protein composition indicative of an epithelial-mesenchymal transition in human micrometastatic and primary breast carcinoma cells. Clin Cancer Res 11:8006-8014.

Wu, F., Fujita, J., Murota, M., Li, J.Q., Ishida, T., Nishioka, M., Imaida, Y., and Kuriyama, S. 2002. CYFRA 21-1 is released in TNF-alpha-induced apoptosis in the hepatocellular carcinoma cell line HuH-7. Int J Oncol 21:441-445.

Wu, F., Nishioka, M., Fujita, J., Murota, M., Ohtsuki, Y., Ishida, T., and Kuriyama, S. 2002. Expression of cytokeratin 19 in human hepatocellular carcinoma cell lines. Int J Oncol 20:31-37.

Yen, Clin Otolaryngol 1998 23: 82-86.

Yokoyama, N., Shirai, Y., Ajioka, Y., Nagakura, S., Suda, T., and Hatakeyama, K. 2002. Immunohistochemically detected hepatic micrometastases predict a high risk of intrahepatic recurrence after resection of colorectal carcinoma liver metastases. Cancer 94:1642-1647.

Zhang, X.W., Yang, H.Y., Fan, P., Yang, L., and Chen, G.Y. 2005. Detection of micrometastasis in peripheral blood by multi-sampling in patients with colorectal cancer. World J Gastroenterol 11:436-438.

International Search Report completed Feb. 14, 2008 for International Application No. PCT/IB2007/002549.

Written Opinion mailed Mar. 19, 2009 for International Application No. PCT/IB2007/002549.

International Preliminary Report on Patentability issued Mar. 10, 2009 for International Application No. PCT/IB2007/002549.

* cited by examiner

FIG. 2A

```
SEQ. ID. NO: 1
  1 MTSYSYRQSS ATSSFGGLGG GSVRFGPGVA FRAPSIHGGS GGRGVSVSSA
 51 RFVSSSSSGG YGGGYGGVLT ASDGLLAGNE KLTMQNLNDR LASYLDKVRA
101 LEAANGELEV KIRDWYQKQG PGPSRDYSHY YTTIQDLRDK ILGATIENSR
151 IVLQIDNARL AADDFRTKFE TEQALRMSVE ADINGLRRVL DELTLARTDL
201 EMQIEGLKEE LAYLKKNHEE EISTLRGQVG GQVSVEVDSA PGTDLAKILS
251 DMRSQYEVMA EQNRKDAEAW FTSRTEELNR EVAGHTEQLQ MSRSEVTDLR
301 RTLQGLEIEL QSQLSMKAAL EDTLAETEAR FGAQLAHIQA LISGIEAQLA
351 DVRADSERQN QEYQRLMDIK SRLEQEIATY RSLLEGQEDH YNNLSASKVL
```

FIG. 2B

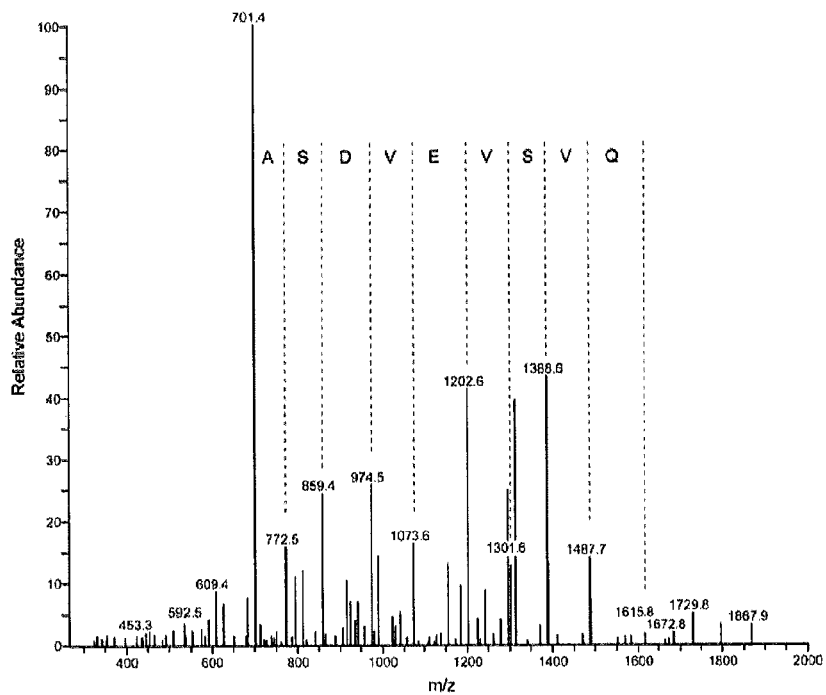

RELEASED CYTOKERATINS AS MARKERS FOR EPITHELIAL CELLS

RELATED APPLICATIONS

This application claims the benefit under 35 U.S.C. §371 of International Application No. PCT/IB2007/002549, filed Sep. 4, 2007, which claims the benefit of U.S. Provisional Application Ser. No. 60/842,902, filed Sep. 7, 2006. These references are incorporated herein in their entirety.

FIELD OF THE INVENTION

The present invention relates to the detection and characterization of cells derived from epithelial tissues, including epithelial tumors.

BACKGROUND

Epithelial cells present in mesenchymal organs (e.g., blood, bone marrow or lymph nodes) can be detected by the expression and/or release of epithelial-specific cytoskeleton proteins called cytokeratins. For example, epithelial tumor cells derived from carcinomas such as breast, prostate, lung or colon cancers may be detected at the single cell level using cytokeratins (Pantel K, Brakenhoff R H, 2004, *Nat Rev Cancer* 4:448-56; Alix-Panabières C, et al., 2007, *Clin Chem* 53:537-9).

Cytokeratins constitute the largest intermediate filament protein subgroup and represent a multigene family with more than 20 different types of polypeptides that are divided into relatively acidic type I (CK9-CK20) and basic type II (CK1-CK8) keratins (Moll R, et al., 1982, *Cell*, 31:11-24.). Cells of normal epithelium express at least one type I and one type II keratin. Cytokeratins form the cytoskeleton of epithelial cells and their main function is to maintain the epithelial cell integrity. The expression of cytokeratins varies with the type of epithelial cells, and usually is maintained in epithelial tumor cells (e.g., breast, colon, prostate cancer, etc.) (Steinert et al., 1988, *Annu Rev Biochem* 57:593-625; Chu et al., 2002, *Histopathology* 40:403-39) although changes may occur in the expression pattern of individual cytoskeletal proteins in human breast carcinoma cells (Willipinski et al., 2005, *Clin Cancer Res* 11:8006-8014.). Extra-cellular cytokeratins are detected either as partially degraded single protein fragments, as small complexes, or as large polymeric protein complexes (Rydlander et al., 1996, *Eur J Biochem* 241:309-14). Multiple mechanisms including abnormal mitosis, spill over of monomeric cytokeratin polypeptides from dividing cells, proteolytic degradation of cytokeratin in apoptotic cells, and/or neovascularisation has been suggested. In addition, extra-cellular cytokeratin fragments may be found circulating in the blood due to infection.

CK19, one of the three main keratins with CK8 and CK18, is found in simple or stratified epithelium and in carcinomas, and has been demonstrated to be stably and abundantly expressed in primary epithelial tumors such as breast, colon, lung and hepatocellular cancer cells, but not in mesenchymal hematopoietic cells. Several studies have shown that upon cell stress induced by apoptosis, type I cytokeratins become substrates for caspase 3 proteases and specifically the proteolysis of full length CK19 by caspase 3 to produce the CK19 soluble fragment, CYFRA 21-1, which is released in supernatant of cultured cells, and in the serum of lung cancer patients (Fuchs et al., 1994, *Annu Rev Biochem* 63:345-82; Coulombe, P A, 1993, *Curr Opin Cell Biol* 5:17-29; Ku N O et al., 1997, *J Biol Chem* 272:33197-203; Dohmoto et al., 2001, *Int J Cancer* 91:468-473; Sheard et al., 2002, *J Cell Biochem* 85:670-677). Moreover, Ding et al., (2004, *Mol Cell Proteomics* 3:73-81) demonstrated that overexpression of intracellular CK19 in hepatocellular carcinoma is related to metastatic behavior. However, the release of the full length (intact) CK19 protein has not been reported.

CYFRA 21-1 measurement in the circulation has been established for monitoring patients with lung cancers and in head and neck cancers (Bodenmuller et al., 1994, *Int J Biol Markers* 9:75-81; Nisman et al., 1998, *Cancer* 82:1850-9; Pujol et al., 1993, *Cancer Res* 53:61-6). Intra-cellular CK19 has been also used as a marker for the detection of micrometastatic cancer cells in the bone marrow, lymph nodes, and peripheral blood by immunocytochemistry (ICC) and RT-PCR (Braun et al., 2000, *N Engl J Med* 2000. 342:525-533; Schoenfeld et al., 1997, *Eur J Cancer* 33:854-861). However, these methods are not able to distinguish between viable and apoptotic cells, and they are not suitable to detect secreted marker proteins.

A need exists for a method of detecting viable epithelial cells that release a full-length cytokeratin. A method of detecting a released, full-length cytokeratin as a marker of disseminated epithelial cells present in a non-epithelial sample is also needed to indicate the presence of tumor cells.

BRIEF SUMMARY

In one aspect of the present invention, a method has been developed for detecting viable disseminated epithelial cells in a sample not normally associated with epithelial cells. The method includes isolating the sample including cells from a patient and culturing the cells for a time sufficient for an epithelial cell-specific marker to be released from the cells where the marker is a substantially full-length cytokeratin. The method further includes detecting the released marker. Detection of the marker indicates the presence of disseminated epithelial cells.

In another aspect of the present invention, a method of identifying a substantially full-length epithelial marker released from viable cells is provided. The method includes isolating cells from a patient and culturing the cells for a time sufficient for the epithelial marker to be released from the cells. The marker is a substantially full-length polypeptide having an enzymatic cleavage site within the full-length polypeptide. The method further includes detecting a portion of the full-length polypeptide, the portion being 5' to the enzymatic cleavage site. Detection of the 5' portion identifies the full-length polypeptide.

In yet another aspect of the present invention, a method of detecting viable epithelial cells is provided. The method includes isolating cells from a patient and culturing the cells for a time sufficient for an epithelial-specific marker to be released from the cells where the marker is a substantially full-length cytokeratin. The method further includes detecting the released marker where detection of the marker indicates the presence of viable epithelial cells.

Advantages of the present invention will become more apparent to those skilled in the art from the following description of the preferred embodiments of the present invention that have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

Embodiments of the present invention will now be described by way of example with reference to the accompanying drawings, in which:

FIG. 2A is the full length CK19 amino acid sequence (SEQ. ID. NO: 1) showing the unique tryptic peptide that distinguishes full length CK19 from CYFRA 21-1 underlined (SEQ. ID. NO: 2); and FIG. 2B MS/MS spectrum of the CK19-specific peptide ([M+2H]$^{2+}$; m/z 1007.86), displaying the y-ion series of this peptide with the reversed partial sequence 'ASDVEVSVQ' (SEQ. ID. NO: 15), which demonstrates that full length CK19 was detected in the cell free supernatant of MCF-7 cells.

DETAILED DESCRIPTION

Figure 1:
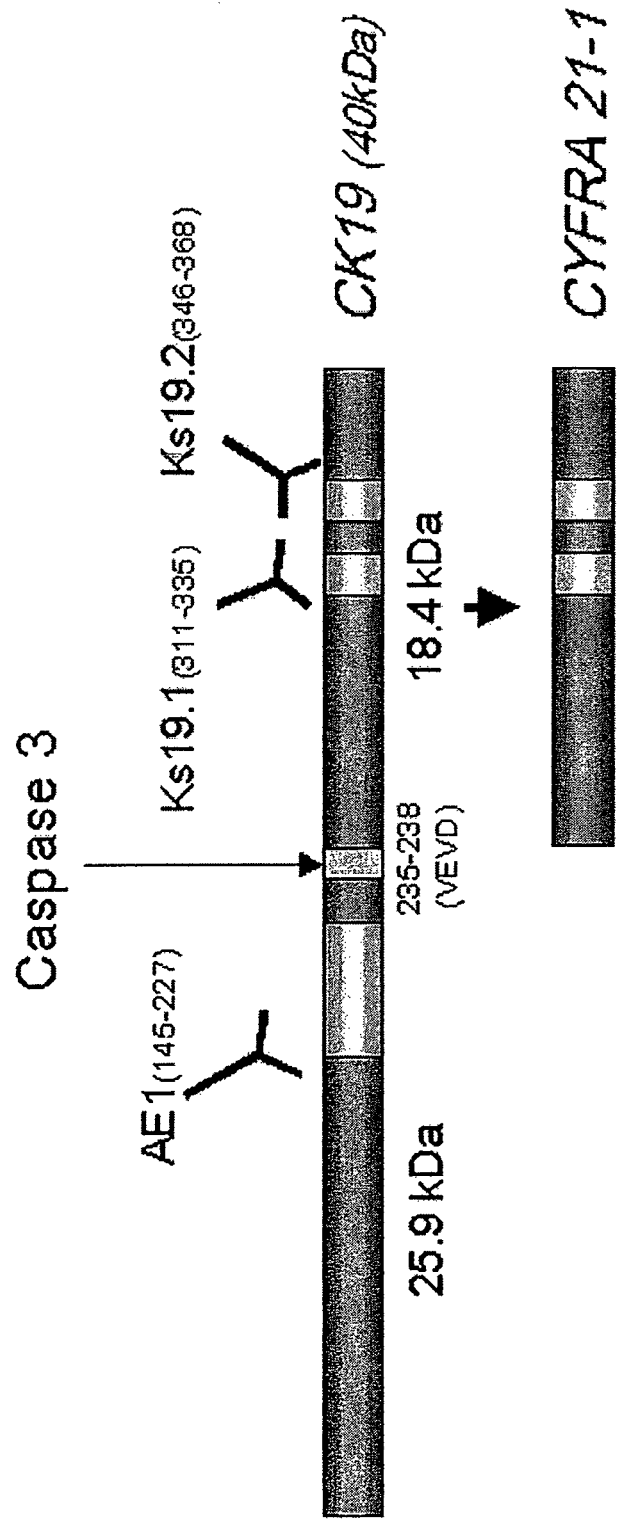
FIG. 1 is a schematic diagram of CK19 illustrating the binding sites of the anti-cytokeratin antibodies and the cleavage site of caspase 3.

The present invention relates to methods of detecting epithelial markers, such as proteins released from viable cells. The methods further include detecting disseminated and circulating epithelial tumor cells. The method may also be used with normal cells expressing epithelial markers. The methods may include detecting markers that are uncleaved, intact proteins, cleaved proteins or otherwise modified proteins released from cells by shedding, secretion or other mechanisms. The methods also relate to detecting disseminated epithelial cells in non-epithelial samples, including mesenchymal tissues such as blood or bone marrow. The term "disseminated" as used herein in reference to a cell means a cell that is found in a location in the body that is different from its site of origin or normal location in the body. Cancer cells that have metastasized are disseminated cells because they have spread from their site or tissue of origin to a different body site. A disseminated cell can also be a cell that has begun to inappropriately express proteins, which may be indicative of a disease state. By way of non-limiting example, an epithelial cell found in the peripheral blood or bone marrow would be a disseminated cell because its site of origin or normal location is other than mesenchymal tissue.

The practice of the present invention will employ, unless indicated specifically to the contrary, conventional methods of immunology, virology, microbiology, molecular biology and recombinant DNA techniques within the skill of the art. Such techniques are explained fully in the literature. See, e.g., Antibodies: A Laboratory Manual, Cold Spring Harbor Laboratory, 1988, Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Ausubel et al., eds., Current Protocols in Molecular Biology, John Wiley & Sons, New York, N.Y. (2000); Glover; ed., DNA Cloning: A Practical Approach, Vols. I & II; Colowick & Kaplan, eds., Methods in Enzymology, Academic Press; Weir & Blackwell, eds., Handbook of Experimental Immunology, Vols. I-IV, Blackwell Scientific Pubs. (1986); Coligan et al., eds., Current Protocols in Immunology, John Wiley & Sons, New York, N.Y. (2000); Animal Cell Culture (R. Freshney, ed., 1986); Perbal, A Practical Guide to Molecular Cloning (1984).

Isolation of Cell Samples

The present invention includes isolating a sample of cells from a patient. The cells may be isolated from any source in the patient. In some aspects, the cells may be isolated from blood, bone marrow, lymph nodes, peritoneal fluid, urine and other sources known to one skilled in the art. Preferably, the cells are isolated from blood, bone marrow or lymph nodes. For example, cells from blood may be isolated from a patient by routine techniques (such as by Ficoll/Hypaque density gradient centrifugation of peripheral blood lymphocytes). Cells from the bone marrow may be isolated using needle aspiration techniques common known in the art. Immunomagnetic beads coated with specific monoclonal antibodies to surface cell markers, or tetrameric antibody complexes, may be used to first enrich or positively select cells, such as circulating tumor cells, in a sample. Various commercially available kits may be used, including Dynabeads™ Epithelial Enrich (Dynal Biotech, Oslo, Norway), StemSep™ (Stem-Cell Technologies, Inc., Vancouver, BC), and RosetteSep™ (StemCell Technologies). A skilled artisan will recognize that other methodologies and kits may also be used to enrich or positively select desired cell populations. Isolated cells may be washed and re-suspended in media and placed into sterile culture in vitro. The isolated cells may be cultured for a time sufficient for the cells to release cytokeratins into the culture media.

Enrichment of Cell Populations within a Sample

In some embodiments of the present invention, the cells may be isolated and depleted of specific populations of cells to further enrich the circulating epithelial cells. For example, CD-45$^+$ cells may be depleted by FACS or by using a commercial kit such as RosetteSep™ including an anti-CD45 antibody to cross link and remove CD-45$^+$ cells such as residual hematopoietic cell lineages. Other cell populations may be depleted using similar techniques known to one skilled in the art.

Released Cytokeratins as Markers Epithelial Cells

In some embodiments of the present invention, the isolated cells may be used in assays to measure epithelial markers expressed by the isolated cells. The epithelial markers may be proteins or fragments thereof that are released by the cells by shedding, secretion, or other mechanisms. The term "epithelial marker" as used herein is broadly defined as any one of a wide variety of proteins peptides, polypeptides, group of peptides or proteins, nucleic acids and related molecules of which the presence or levels of are used to assess the presence of epithelial cells. In some embodiments, the epithelial marker is used to assess the presence of disseminated epithelial cells found in tissues not normally associated with epithelial cells, such as in mesenchymal tissues (e.g. blood, bone marrow), in order to assess the status of tumor progression (in particular, early detection of metastasis) in cancer patients. The epithelial markers can have any structure or configuration, and can be in any location within a cell, on the cell surface or released from the cell. Epithelial markers can be a single polypeptide chain or peptide fragments of a polypeptide. Epithelial markers can also have any secondary structure combination, any tertiary or quaternary structure.

In some embodiments, the epithelial markers may be cytokeratins selected from cytokeratins CK1-CK20. The cytokeratins CK1-CK20 have been described in the literature, for example, see Moll R, et al., 1982, *Cell* 31:11-24, which is incorporated by reference in its entirety herein. In some embodiments, the cytokeratins may be released from the cells. The cytokeratins may be cleaved and a portion of the full-length polypeptide may be released, such as the carboxy terminus. For example, the carboxy terminus of CK-19 may be released after cleavage with caspase 3 as shown in FIG. 1. The cytokeratins may be released as substantially intact, full-length polypeptides that have not been cleaved or otherwise degraded. Intact, full-length cytokeratins may be released by viable cells and have not been cleaved, for example, by an apoptotic enzyme. In some embodiments, the cytokeratin used as an epithelial cell marker may be cytokeratin 19 and further may be cytokeratin 19 that is released from the viable cells as a substantially full-length polypeptide.

The term "substantially full-length" in the context of a released epithelial marker refers to a percentage of amino acid residues that are released from the cell compared to the full-length sequence (i.e., at least about 80%, 85%, 90%, 91%, 92%, 93%, 94%, 95%, 96%, 97%, 98% or 99%).

Additional epithelial markers known to one skilled in the art may also be used.

Detection of Epithelial Cell Markers

The present invention allows for the detection of epithelial cell markers that have been released from isolated cells. In some embodiments, the detection of epithelial cell markers is in a population of mixed cells, such as epithelial cells and mesenchymal tissues, where the epithelial cells may be disseminated tumor cells. For example, the epithelial cell markers may be detected in a population of mesenchymal cells that do not normally include epithelial cells where the epithelial cell marker indicates disseminated epithelial tumor cells. In some embodiments, the detection of epithelial cell markers is within a population of normal cells.

The methods for detecting expression of epithelial markers, in particular cytokeratin expression, encompass the whole range of conventional diagnostic methods. Examples thereof are microscopic, immuno-cytological/immunocytochemical, biochemical and/or molecular biological methods. For example, methods for detecting released epithelial marker proteins may include, but are not limited to, Enzyme-Linked Immunosorbant Assays, ELISPOT assays, Western blot, radioimmunoassays, protein microarrays, and proteomics assays, including mass spectrometry.

Immunoassays suitable for detection of the epithelial markers typically include contacting a test sample with an antibody that specifically binds to or otherwise recognizes a marker, and detecting the presence of a complex of the antibody bound to the marker in the sample. Polyclonal or monoclonal antibodies may be used. The antibody may be fixed to a solid support prior to contacting the antibody with a test sample to facilitate washing and subsequent isolation of the antibody/protein marker complex. Examples of solid supports include, for example, glass or plastic in the form of, for example, a microtiter plate. Antibodies can also be attached to the probe substrate, such as the protein arrays.

After incubating the test sample with the antibody, the mixture is washed and the antibody-marker complex may be detected. The detection can be accomplished by incubating the washed mixture with a detection reagent, and observing, for example, development of a color or other indicator. Any detectable label may be used. The detection reagent may be, for example, a second antibody which is labeled with a detectable label. Exemplary detectable labels include magnetic beads (e.g., DYNABEADS™), fluorescent dyes, radiolabels, enzymes (e.g., horseradish peroxidase, alkaline phosphatase and others commonly used in enzyme immunoassay procedures), and colorimetric labels such as colloidal gold, colored glass or plastic beads. Alternatively, the marker in the sample can be detected using an indirect assay, wherein, for example, a labeled antibody is used to detect the bound marker-specific antibody complex and/or in a competition or inhibition assay wherein, for example, a monoclonal antibody which binds to a distinct epitope of the marker is incubated simultaneously with the mixture. The amount of an antibody-marker complex can be determined by comparing to a standard.

In some embodiments, the released epithelial marker may be detected using an antibody directed to a 5' portion of a polypeptide that is upstream of a known cleavage site to detect a substantially full-length released epithelial marker. For example, the 5' antibody may be upstream of an apoptotic cleavage site, such as a caspase family member site. An antibody directed to a 3' portion of a polypeptide may also be used, preferably together with the 5' antibody to detect substantially full-length released epithelial markers.

Such assays are well-known to the skilled artisan and are described, for example, more thoroughly in Antibodies: A Laboratory Manual (1988) by Harlow & Lane; Immunoassays: A Practical Approach, Oxford University Press, Gosling, J. P. (ed.) (2001) and/or Current Protocols in Molecular Biology (Ausubel et al.) which is regularly and periodically updated.

The epithelial markers identified in the assay may be used to identify disseminated tumor cells derived from solid tumors. Examples of solid tumors that may be identified by the epithelial markers include, but are not limited to the following: carcinoma, adenoma, hepatocellular carcinoma, hepatoblastoma, esophageal carcinoma, thyroid carcinoma, ganglioblastoma, synovioma, Ewing's tumor, colon carcinoma, pancreatic cancer, breast cancer, ovarian cancer, prostate cancer, squamous cell carcinoma, basal cell carcinoma, adenocarcinoma, renal cell carcinoma, bile duct carcinoma, melanoma, choriocarcinoma, seminoma, embryonal carcinoma, Wilms' tumor, cervical cancer, testicular tumor, lung carcinoma, small lung carcinoma, bladder carcinoma, epithelial carcinoma, craniopharyngioma, ependymoma, pinealoma, retinoblastoma, rectal carcinoma, cancer of the thyroid, head and neck cancer, and cancer of the endometrium.

The invention is further illustrated by way of the following examples, which are intended to elaborate several embodiments of the present invention. These examples are not intended to, nor are they to be construed to limit the scope of the invention. Those skilled in the art will recognize, or be able to ascertain, using no more than routine experimentation, numerous equivalents to the specific substances and procedures described herein. Such equivalents are intended to be encompassed in the scope of the claims that follow the examples below.

EXAMPLES

Cell Preparation

Patients and healthy controls. After written informed consent was obtained, 10 metastatic colon cancer patients, 13 localized cancer patients and 11 patients presenting a benign colorectal disease were included in this study at the Department of Gastroenterology Surgery at the Saint-Eloi Hospital of Montpellier, as well as 14 cancer-free volunteers. None of the patients had received chemotherapy or radiotherapy during the months preceding the study. In addition, we included 57 breast cancer patients at different stages (20 metastatic and 37 localized breast cancer patients) at the Val d'Aurelle Clinic of Montpellier, as well as 11 patients with a lymphoma as the negative control group.

In order to explore the normal mammary cells in the milk, 3 healthy lactating women were recruited with the help of the Human Milk Bank of the University Hospital of Montpellier, France.

Hematopoietic cell depletion procedure. Blood samples collected into EDTA tubes were depleted of hematopoietic cell using the RosetteSep® procedure (RosetteSep Circulating Epithelial Tumor Cell Extensive Enrichment Cocktail, StemCell, Vancouver, Canada, according to the manufacturer's instructions. Cells were then cryopreserved in liquid nitrogen before testing them with the CK19-EPISPOT assay (described below).

Isolation of normal primary mammary cells from milk samples. Whole milk was centrifuged at 1200×g for 15 min at 4° C. to remove acellular and lipid fractions. Breast Milk Cell (BMC) pellets were washed three times in phosphate-buffered saline (PBS) supplemented with 5% FCS. Then, the cells were resuspended in the complete DMEM medium described below for MCF-7 cells. Non-hematopoietic cells were isolated from BMC aliquots of controls lactating women by negative selection using a rosetting process. Briefly, red blood cells were isolated from 5 ml of whole blood from healthy donors by centrifugation of the sample for 10 min at 50×g to remove the peripheral blood mononuclear cells (PBMC). Red blood cells were washed three times in PBS-2% FCS and were resuspended in 1 ml of PBS-2% FCS. Hundred microliters of red blood cells was then added to 3 ml of the BMC suspension. $CD45^-$ cells were then separated from BMC using a RosetteSep™ CD45 negative cell enrichment cocktail including tetrameric complexes with antibodies (Abs) directed against membrane receptors of human hematopoietic cells (CD2, CD16, CD19, CD36, CD38, CD66b and CD45) and of red blood cells (glycophorin A) (Stemcell Technologies, Meylan, France). Briefly, BMC and red blood cells were incubated for 20 min at room temperature with the antibody enrichment cocktail, and then layered on ficoll-hypaque density gradient by centrifugation for 20 min at 1200×g. Enriched resting non-hematopoietic $CD45^-$ cells were recovered from ficoll/plasma interface, washed three times in PBS-2% FCS and resuspended in the complete DMEM medium with FCS and antibiotics.

Preparation of cells from normal and tumor colon tissue. Human normal and tumor colon tissue specimens were received from the operating room in tubes containing DMEM with 10% FCS and antibiotic drugs and were kept on ice until disaggregation. We examined 2 primary colon carcinomas and 2 normal colon tissues. Colon tissue was mechanically disaggregated by means of automated tissue disaggregator Medimachine (DAKO, Hamburg, Germany). For this purpose, tumor tissue was cut into small pieces and placed into a disposable disaggregation chamber (Medicon; DAKO) together with 1.5 ml of serum-free invasion medium (DMEM with 2 mmol/L 1-glutamine, antibiotic drugs, and 0.1% bovine serum albumin (BSA; Sigma)). The Medicon was inserted into the motor unit of the machine and run for 2 minutes at a pre-fixed rotation speed of approximately 80 rpm. An aliquot of the cell suspension containing single cells and cell clusters was counted in a Kova slide hematocytometer with Trypan blue dye exclusion staining.

Cell Lines

Colorectal (HT-29, Caco-2 and HCT 116) and mammary (MCF-7) adenocarcinoma cell lines were used as positive controls for the optimization of the CYFRA 21-1- and CK-19-EPISPOT assay. Head and neck squamous cancer cell lines (SCC-14C and SCC-22A) were kindly provided by Pr R. H. Brakenhoff (Dept. Otolaryngology/Head-Neck Surgery, Amsterdam, Netherlands). The ML-1 and the C643 thyroid cancer cell lines were kindly provided by Dr D. Grimm (Department of Nuclear Medicine, University of Regensburg, Germany) and Dr N-E Heldin (Department of Genetics and Pathology, Uppsala University Hospital, Uppsala, Sweden), respectively. The prostate cancer cell lines LNCaP and PC3 were also used in the development of this assay.

HT-29 and HCT 116 cells were maintained in Mc Coy's 5A medium (Invitrogen, Leiden, The Netherlands) supplemented with 1% glutamax (Life Technologies, Paisley, Scotland), 10% fetal calf serum (FCS, Life Technologies), 500 U/mL penicillin, and 500 µg/mL streptomycin (Life Technologies) in a humidified incubator containing 5% $CO_2$ at 37° C. Caco-2 and C643 cells were maintained in minimal essential medium (Eurobio) supplemented with 1% glutamax (Life Technologies), 20% FCS (Life Technologies), 500 U/ML penicillin, and 500 µg/mL streptomycin (Life Technologies). MCF-7, ML-1, SCC-14, SCC-22, PC3 and LNCaP cells were maintained in Dulbecco's modified Eagle's medium (DMEM, Biochrom KG, Berlin, Germany) supplemented with 1% glutamax (Life Technologies, Paisley, Scotland), 10% FCS (Life Technologies), 500 U/mL penicillin, and 500 µg/mL streptomycin (Life Technologies) in a humidified incubator containing 5% $CO_2$ at 37° C.

Assays

Measurement of CYFRA 21-1. CYFRA 21-1 was measured by the CYFRA 21-1 immunometric assay (B.R.A.H.M.S., Hennigsdorf, Germany) in culture supernatants. The threshold of detection of this assay was 0.05 ng/mL. Values are expressed as means±SD from 3 separate determinations.

EPISPOT assays. Immobilon-P membrane 96-well plates (MAIPN450, Millipore Corporation, Bedford, Mass.) were coated overnight at 4° C. with the anti-CK19 mAb Ks19.1 (6 µg/mL) (Progen Biotechnik GMBH, Heidelberg, Pa.). Unbound mAb were removed by washing three times with PBS. The plates were then blocked with PBS supplemented with 5% FCS (Sigma, Chemical Co., Saint Louis, Mo.) for 1 h at room temperature and washed three times with PBS. To block protein synthesis, cell lines were incubated with 50 µg/mL of cycloheximide during the EPISPOT assay. Subsequently, viable cells were counted in a Kovac slide with trypan blue dye exclusion staining and finally plated in three replicate wells at different concentrations ($1 \times 10^5$, $1 \times 10^4$, $1 \times 10^3$, $1 \times 10^2$, 10 and 1 cells). In addition, $5 \times 10^4$ to $1 \times 10^5$ of enriched $CD45^-$ cells (i) from blood and bone marrow of colon and breast cancer patients, respectively, (ii) from the milk of healthy lactating women (normal primary mammary cells) or (iii) from normal and tumor colon tissues were seeded in different wells of the plates. After 24-48 h of cell-culture at 37° C. in 5% $CO_2$, cells were removed by washing six times with PBS containing 0.2% Tween-20 and three times with PBS alone, then the $Alexa^{488}$ conjugated-anti-CK19 mAb Ks19.2 (3 µg/mL) (Progen Biotechnik GMBH) and/or the $Alexa^{555}$ conjugated-anti-CK19 mAb AE1 (3 µg/mL) (Chemicon international, Cemecula, Calif., USA) were added (100 µl/well), and the plates were incubated overnight at 4° C. The green- and the red-fluorescent spots represented cells secreting CYFRA 21-1 and the intact full length CK19 protein, respectively. Immunospots were counted by video camera imaging and computer assisted analysis (KS ELISPOT, Carl Zeiss Vision, Halbermoos, Germany). Each experiment was performed in triplicate. Quality control was performed under standardized EPISPOT assay conditions by including in each experiment a positive control ($5 \times 10^2$ MCF-7 cells in triplicate) and three negative controls (wells without cells and wells without the addition of the coating mAbs or the secondary mAbs).

For the dual fluorescent CK19/MUC1-EPISPOT assay, membranes of 96-well plates were coated overnight at 4° C. with a mixture of anti-CK19 mAb Ks19.1 (6 µg/mL) and anti-MUC1 mAb 115D8 (5 µg/mL) (Centocor, Malvern, Pa.). The revelation step was performed with a mixture of Alexa$^{488}$ conjugated-anti-CK19 mAb Ks19.2 (3 µg/mL) and anti-MUC1 mAb DF3 (1/3000) (Centocor) (100 µl/well), and the plates were incubated overnight at 4° C.

The labeling of all the monoclonal mAb used in this study was realized using the Alexa Fluor$^{488}$ or Alexa Fluor$^{555}$ Monoclonal Antibody Labelling Kit (Molecular Probes, Invitrogen) according to the manufacturer's recommendations.

Flow cytometry experiments. The percentage of CK19-positive cell lines was determined by flow cytometry (FC 500 apparatus; Beckman-Coulter, Villepinte, France). Intra-cytoplasmic CK-19 staining was performed by using the Alexa$^{488}$- or Alexa$^{555}$-conjugated monoclonal anti-human CK-19 mAb Ks19.2 (Progen Biotechnik GMBH), and the IntraPrep™ permeabilization reagent kit, according to the manufacturer's recommendations (Beckman-Coulter).

Cytospin preparation and double immunocytochemical staining. All the cell lines (breast, prostate, thyroid and colorectal cancer cell lines) were immunostained with Alexa$^{488}$- conjugated anti-CYFRA 21-1 mAb as described above for the flow cytometry experiments. After this step, cells were seeded on glass slides using a Cytospin 4 centrifuge (Shandon, Runcorn, England). Slides were finally mounted in ProLong Gold antifade reagent with DAPI (Molecular Probes) and analyzed by video camera imaging and computer assisted analysis (Axio Imager M1 with the AxioVision software, Carl Zeiss Vision, Halbermoos, Germany).

For some experiments, MCF-7 cells were incubated with or without vincristin 20 µM (Sigma-Aldrich, Steinheim, Germany). Cells were recovered after 5, 16, 24, 36 and 48 hours and a dual immunostaining was performed using (i) the M30 CytoDEATH™ Fluorescein (Peviva, Bromma, Sweden) according to the manufacturer's recommendations, then (ii) the Alexa$^{555}$-conjugated anti-CYFRA 21-1 mAb Ks19.2 as described above. Red and green cells corresponding to CYFRA 21-1-staining and to M30 CytoDEATH-staining, respectively, were analyzed by microscopy. Each nuclear compartment was stained in blue with DAPI.

For other experiments, a dual immunostaining was performed on MCF-7 cells using the Alexa$^{488}$-conjugated anti-CYFRA 21-1 mAb Ks19.2 and the Alexa$^{555}$-conjugated anti-MUC1 mAb DF3. Green and red cells corresponded to CYFRA 21-1-staining and to MUC1-staining for breast cells, respectively. Each nuclear compartment was stained in blue with DAPI.

Western blot. To detect the presence of CK19 in cell lines, cells of a 75 cm$^2$ flask were lysed in 5 mL of Triton-DOC lysis buffer for 5 min. After 1 min centrifugation at 10,000 rpm, the supernatant was collected and analysed by Western blotting. The samples were then mixed with an equal volume of 2× Laemmli buffer, boiled for 5 min and then loaded on to a 12% polyacrylamide gel. Proteins were electroblotted on to Immobilon membranes and CK19 was detected by using the anti-CK19 KS 19.2 Alexa$^{488}$ antibody. The Immobilon membrane was scanned with Phosphorimageur (Typhoon).

Preparation of the protein samples for analysis with mass spectrometry. MCF-7, PC3, and C643 cells were cultured in FCS-free medium and test with the ELISPOT assay to confirm that full length CK19 still could be detected. Medium without FCS was used as negative control. Five mL of each cell culture supernatant was concentrated using 5 kDa cut-off centrifugal filter units (Millipore, Amsterdam, the Netherlands). The concentrated supernatants were diluted with 50 mM ammonium bicarbonate (pH 8) in a total volume of 50 µL and digested with 1 µg trypsin at 37° C. for 15 h. Hydrophobic proteins attached to the centrifugal filter unit were digested with 1 µg trypsin in 50 µl 10% (v/v) acetonitril in 50 mM ammonium bicarbonate (pH 8) at 37° C. for 4 h. Samples were cleaned of salts using STAGE tips (Rappsilber, J., et al. 2003. *Anal Chem* 75:663-670.).

LC-MS/MS analysis and protein identification. Nanoscale LC-MS/MS was performed by coupling an Agilent 1100 Series LC system to a LTQ XL™ quadrupole ion trap mass spectrometer (Finnigan, San Jose, Calif.). Peptide mixtures were concentrated and desalted using an on-line C18 trap column (OD 375 µm, ID 100 µm packed with 20 mm of 5 µm AQUA C18, RP particles (Phenomenex, Torrance, Calif.)) and further separation was achieved by gradient elution of peptides onto a C18 reverse phase column (OD 375 µm, ID 50 µm packed with 15 cm of 3 µm C18, Reprosil RP particles (Dr. Maisch, Ammerbuch-Entringen, Germany)). MS detection in the LTQ was achieved by directly spraying the column eluent into the electrospray ionization source of the mass spectrometer via a butt-connected nano-electrospray ionization emitter (New Objective, Woburn, Mass.). Mobile phase buffers were A: 0.1 M acetic acid, and B: 80% acetonitrile, 0.1 M acetic acid. A linear 30 min gradient (0-50% B) was applied for peptide elution into the MS at a final flow rate of 100 nl/min. The total analysis time was 1 h per sample. The LTQ was operated in the positive ion mode, and peptides were fragmented in data-dependent mode. One mass spectrometry survey zoom scan was followed by three data dependent MS/MS scans.

To identify the proteins, all spectra from each LC-MS run were merged to a single file which was searched using the Mascot search engine (Matrix Science) against the human NCBI-nr protein database with carbamidomethyl cysteine as fixed modification, and oxidized methionine as variable modification. Trypsin was specified as the proteolytic enzyme and a maximum of one missed cleavage was allowed. The peptide mass tolerance was set to 0.5 Da, and the MS/MS tolerance to 0.9 Da.

Results

Enumeration of cells releasing the CYFRA 21-1. A soluble fragment of CK19 named CYFRA 21-1, can be measured using two mouse monoclonal anti-CK19 antibodies, clones Ks19.1 (recognizing the amino acids from 311 to 335) and Ks19.2 (recognizing the amino acids from 346 to 368) (FIG. 1). The KS19.1 and KS19.2 antibodies and different cancer cell lines (MCF-7 mammary, and HT-29, HCT116, Caco-2 colorectal cancer cell lines) were used to optimize a CYFRA 21-1$^{(Alexa488)}$-EPISPOT assay. In total, 21.5% (range 19.8-25), 88.2% (range 73-100), 55.6% (range 40-67.5) and 17% (range 11.4-23) of HT-29, HCT 116, Caco-2 and MCF-7 cells, respectively, released CYFRA 21-1 after 24 hours of cell-culture (n=4). To determine the sensitivity of this EPISPOT assay, serial dilutions of the HT-29, HCT 116, Caco-2 and MCF-7 cell lines [1×10$^4$, 1×10$^3$, 1×10$^2$, 10 and 1 cell(s) per well] were tested. In parallel, CYFRA 21-1 was measured by an immunometric assay on the corresponding supernatants (Table 1). When 1×10$^4$ of HT-29, HCT 116, Caco-2 and MCF-7 cells were seeded per well, the spots were so numerous that they could not be counted by the automated reader, but 21.9±12.9, 24.3±9.8, 163.3±63.4 and 156.2±10.8 ng/mL of CYFRA 21-1 were quantified in culture supernatants, respectively. At a concentration of 10 of HT-29, HCT 116, Caco-2 and MCF-7 cells per well, 2.0±0.0, 7.3±1.8, 5.5±0.5 and 2.0±0.7 spots of CYFRA 21-1-releasing cells (RC) were counted, whereas released CYFRA 21-1 were not detected in the corresponding culture supernatants. These data demonstrate that the sensitivity of the CYFRA 21-1-EPISPOT assay is two orders of magnitude greater compared with the quantification of these proteins in the cell-free supernatants. Taken together, these results indicate that the CYFRA 21-1-EPISPOT assay permitted the enumeration of a very small number of CYFRA 21-1-RC.

In addition, experiments were performed with prostate (LNCaP), head and neck squamous (UM-SCC-22A, UM-SCC-14C), and thyroid (ML-1, C643) cells which do not express the CK19 and consequently no CYFRA 21-1-RC was observed. The expression of CK19 was measured in these cell lines by flow cytometry, immunocytochemistry (ICC) and western-blot (WB) experiments. The PC3 prostate cell line was also studied. These cells expressed weakly the CK19 as shown by flow cytometry, ICC and WB experiments, but CK19 release by PC3 cells was not observed as demonstrated by the CYFRA 21-1-EPISPOT assay and the CYFRA 21-1 immunometric assay. Excepted prostate, thyroid and head and neck squamous cancer cell lines, all the other epithelial cancer cells tested (breast and colon tumor cells) released CYFRA 21-1 in their supernatants as shown by the measure of this protein in the cell-free supernatants.

Enumeration of cells releasing the intact full length CK19 protein. Several groups hypothesized that the release of CYFRA 21-1 occurs when CK19 is cleaved by caspase 3 during the apoptosis (Dohmoto, K., et al. 2001, *Int J Cancer* 91:468-473; Wu, F., et al. 2002, *Int J Oncol* 21:441-445.). To demonstrate that the protein detected was the substantially intact full length CK19 protein and not its soluble fragment, a CK19$^{(Alexa\ 555)}$-EPISPOT assay was developed in parallel of the CYFRA 21-1$^{(Alexa\ 488)}$-EPISPOT assay. For the full length CK19 assay, the same cell lines than those cited above were used as well as the same coating anti-CK19 antibody Ks19.1 which recognizes an epitope on the CYFRA 21-1 fragment of the CK19 (recognizing the amino acids from 311 to 335) (FIG. 1). For the revelation step of this CK19-EPISPOT assay another antibody, AE1, which recognizes the CK19 on a different epitope, localized on the 5' side of the cut site of the caspase 3 (recognizing the amino acids from 145 to 227), was used (FIG. 1). Similar percentages of CK19-RC were detected compared to those observed with the CYFRA 21-1 EPISPOT assay. A dual fluorescent CYFRA 21-1$^{(Alexa488)}$/CK19$^{(Alexa\ 555)}$-EPISPOT assay was used, allowing the enumeration of cells releasing one or both proteins: the CYFRA 21-1 soluble fragment and/or the full length CK19 protein. This dual fluorescent EPISPOT assay clearly demonstrated that only dual$^{yellow}$ immunospots were observed, confirming that the immunospots are the fingerprints of cells releasing only one protein: the intact full length CK19 protein, detected by both anti-CK19 Abs (AE1$^{(Alexa\ 555)}$, specific of the full length CK19 protein and Ks19.2$^{(Alexa488)}$, located on the CYFRA 21-1 fragment of the CK19 protein.

Enumeration of viable cells. As described above, it has been reported that the CK19 was released by apoptotic or necrotic cells. Experiments were performed with cycloheximide, an inhibitor of the protein translation, in cell-cultures during the incubation step of the CK19-EPISPOT assay. The addition of cycloheximide led to a decrease in the size and the number of spots, confirming the de novo synthesis of the CK19 protein by viable epithelial cells.

Moreover, experiments with PC3 cells showed expression but never release of CK19. These experiments demonstrated that cells were viable and not apoptotic otherwise CK19-immunopots would have been detected even for these CK19-expressing but not releasing cells.

Enumeration of viable cells releasing simultaneously MUC1 and CK19. Moreover, as viable MCF-7 cells were already demonstrated as MUC1-releasing cells (Alix-Panabieres, C., et al., 2005, *J Immunol Methods* 299:177-188.), a dual fluorescent MUC1$^{(Alexa\ 555)}$/CK19$^{(Alexa\ 488)}$-EPISPOT assay was optimized to verify whether these cells were able to release both proteins simultaneously. A majority of the immunospots obtained after 24 hours of cell-culture observed were yellow-staining, resulting of an equivalent mixture of the released MUC1 and CK19 proteins and confirming that these RC were viable cells able to neosynthetize in vitro MUC1 and/or CK19.

Intracellular localization of CK19 in non-apoptotic cells. The expression of CK19 was investigated by ICC experiments on different cell lines. LNCap cells were not immunostained for CK19 whereas MCF-7 expressed CK19 protein. Even after a cell-incubation with vincristin, an inducer of apoptosis, some of the MCF-7 cells were still viable and showed an immunostaining for CK19 in intra-cytoplasmic vesicles without any staining with the antibody M30 CytoDEATH™ which recognizes a neo-epitope formed after caspase cleavage of cytokeratin 18 at Asp396 (CK18Asp396-NE M30 neo-epitope) (Leers, M. P., et al. 1999, *J Pathol* 187:567-572.) during and after apoptosis. As M30 CytoDEATH™ does not bind native CK18 of normal cells, it is a very reliable and convenient tool for demonstration of apoptosis in single cells. In additional experiments, it was shown that viable MCF-7 cells had CK19 vesicles with a peripheral MUC1 expression at the cell membrane, confirming the results obtained with the dual fluorescent MUC1$^{(Alexa\ 555)}$/CK19$^{(Alexa\ 488)}$-EPISPOT assay.

Release of CK19 by normal mammary primary cells. Isolation of non-hematopoietic cells purified from EDTA-treated blood samples was adapted to breast milk samples. Normal mammary cells were purified from breast milk cells (BMC) of three healthy lactating women and then analyzed by flow cytometry and EPISPOT assay. As previously described, the CD45-negative cells is the major population in BMC (mean=93.5%, range 88.5-97.9) (Petitjean, G., et al., 2007, *J Clin Virol* 39:1-8.). More than 72.4% of these cells were found to express the EpCAM membrane marker and defined as mammary epithelial cells. When 550,000 CD45-negative cells were analyzed by the CK19-EPISPOT assay, 320 CK19-RC were detected (0.06%), showing that a small subset of these normal mammary cells were viable by releasing the full length CK19 protein.

Release of CK19 by normal and cancer cells from colon tissue. Cells extracted from the tumor and the normal mucous of three patients with a colorectal cancer released CK19 as observed with CK19-EPISPOT assay experiments (data not shown).

Detection of CK19-RC added to blood from healthy donors. When the ELISPOT assay was performed on peripheral blood mononuclear cells (PBMC) from 14 healthy donors, no cells releasing CK19 were detected. As described previously for breast and prostate cancer cells (Alix-Panabieres, C., et al., 2005, Clin Chem 51:1538-1541.), when 100 and 10 HT-29 cells were dispersed in 10 ml of normal human blood and depleted of hematopoietic cells, the efficacy for recovery of CK19-releasing HT-29 cells dispersed in control blood was 41.9%, 88.2%, respectively. The combination of the cell preparation procedure and the CK19-EPISPOT assay was found to be more efficient for the low HT-29 cell densities.

Release of CK19 by CTC/DTC in colon cancer patients. Non-hematopoietic cells were isolated from blood samples collected in EDTA tubes (15 ml) and the single fluorescent CK19-EPISPOT assay performed as described above. CK19-RC were detected in the peripheral blood of 40% of the patients with metastatic colon cancer (n=10) and 15.3% of the patients with localized colon cancer (n=13) whereas no such cell was found in the blood of patients with a benign colon disease (n=11) nor in HC (n=14). Among the positive samples, the median frequency of RC was 3 (range 1-6) and 2 (range 1-3) for metastatic and localized colon cancer patients, respectively. The finding that CK19-RC were present in patients with a metastatic or localized colon cancer and not in patients with a benign colon disease nor in healthy controls suggest that these cells are viable circulating tumor cells released from the primary tumor.

Results on Samples from Breast Cancer Patients

The results of the CK19-ELISPOT assay on breast cancer patient samples (5 ml of bone marrow) are shown in Tables 1A and 1B. The enumeration of CK19-SC allowed the detection of viable disseminated tumor cells in 70% and 45.9% of M1 and M0 patients, respectively. Moreover, the number of disseminated tumor cells per sample was considerably lower in the M0 patients compared to the M1 patients. In contrast, no CK19-SC was detected in the bone marrow of the control group (patients with lymphoma), suggesting strongly that the CK19-SC in the patients with breast cancer probably represented cells derived from the primary tumor and are the disseminated tumor cells, as already reported (Allard et al., 2004, *Clin Cancer Res* 10:6897-6904.).

Figure 3:
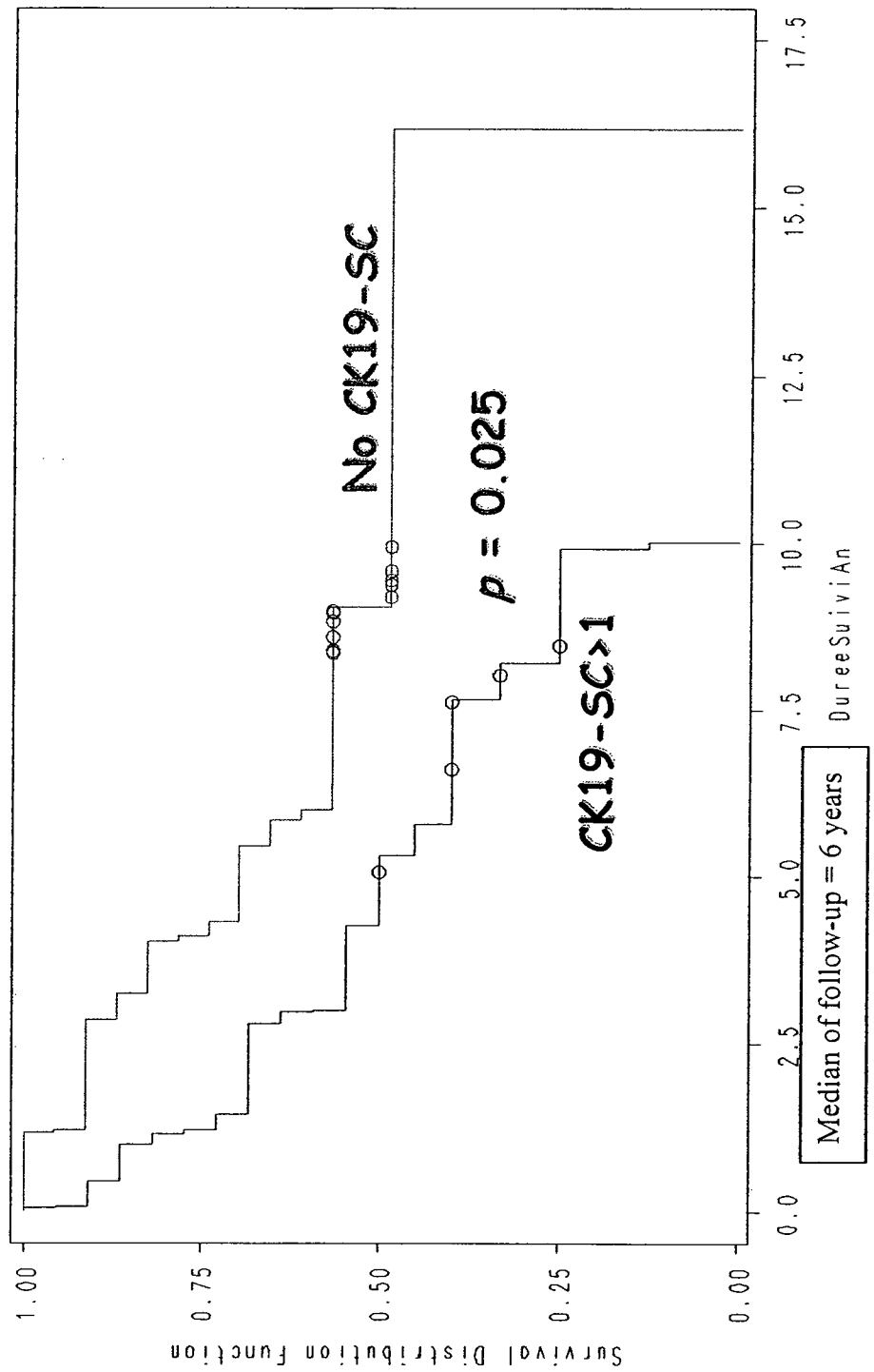
FIG. 3 illustrates Kaplan-Meier analyses performed with breast cancer patients followed up for a median of 6 years. Patients with epithelial cells secreting CK19 in their bone marrow had an unfavorable clinical outcome, indicating that these cells might be tumor cells capable of forming overt metastases in the bone and other secondary organs such as liver, lung or brain. Thus these data provide evidence of the malignant potential of disseminated epithelial tumor cells secreting CK19.

Kaplan-Meier analyses were performed with these breast cancer patients followed up for a median of 6 years (FIG. 3). The survival curves showed a significant difference between the breast cancer patients with and without CK19-SC in their bone marrow (p=0.025, log Rank test). These results demonstrate that CK19-SC is an important and biological active subset of disseminated tumor cells.

TABLE 1A

CK19-ELISPOT assay on bone marrow samples from 20 patients with metastatic breast cancer (M1 patients)

| M1-patients | CK19+-SC[1] |
|---|---|
| 1 | 1 |
| 2 | 6 |
| 3 | 0 |
| 4 | 49 |
| 5 | 57 |
| 6 | 271 |
| 7 | 102 |
| 8 | 168 |
| 9 | 0 |
| 10 | 0 |
| 11 | 0 |
| 12 | 8 |
| 13 | 758 |
| 14 | 9 |
| 15 | 19 |
| 16 | 0 |
| 17 | 142 |
| 18 | 0 |
| 19 | 2 |
| 20 | 1 |
| Total n DTC[2] | 1593 |

SC[1]: Secreting Cells
DTC[2]: Disseminated Tumor Cells

TABLE 1B

CK19-ELISPOT assay on bone marrow samples from 37 patients with localized breast cancer (M0 patients) (a), and from 10 patients with a lymphoma, the control group (b).

| M0-patients | CK19+-SC[1] |
|---|---|
| a. | |
| 21 | 254 |
| 22 | 1 |
| 23 | 92 |
| 24 | 0 |
| 25 | 0 |
| 26 | 159 |
| 27 | 0 |
| 28 | 0 |
| 29 | 0 |
| 30 | 0 |
| 31 | 3 |
| 32 | 1 |
| 33 | 0 |
| 34 | 0 |
| 35 | 0 |
| 36 | 0 |
| 37 | 0 |
| 38 | 0 |
| 39 | 2 |
| 40 | 0 |
| 41 | 1 |
| 42 | 0 |
| 43 | 28 |
| 44 | 2 |
| 45 | 11 |
| 46 | 23 |
| 47 | 6 |
| 48 | 1 |
| 49 | 0 |
| 50 | 7 |
| 51 | 0 |
| 52 | 0 |
| 53 | 0 |
| 54 | 6 |
| 55 | 0 |
| 56 | 2 |
| 57 | 0 |
| Total in DTC[2] | 599 |
| b. | |
| Control Group (n = 10) | 0 |

SC[1]: Secreting Cells
DTC[2]: Disseminated Tumor Cells

Detection of the full length CK19 with tandem mass spectrometry. The secretion of full length CK19 protein (400 amino acids; FIGS. 2A and 2B, SEQ. ID. NO:1, SEQ. ID. NO: 15) by MCF-7, PC3 and C643 cells was also investigated with peptide sequencing using nanoscale reversed phase liquid chromatography tandem mass spectrometry (LC MS/MS analysis). The CK19 protein was only identified in the MCF-7 cell free supernatant sample, and not in the PC3 and C643 cell free supernatant samples. The CK19 was only detected at a low level in the flow cytometry and ICC experiments, which may explain lack of detection with the less sensitive LC MS/MS method. As can be seen from Table 2, CK19 in the MCF-7 cell free supernatant was detected with peptides ranging from amino acid 254 to 381. This may refer to intact CK19 as well as the CYFRA 21-1 product (FIG. 8A), since CYFRA 21-1 shares residues 238-400 with CK19. Conversely, the tryptic fragment peptide 'DSAPGTDLAK' (SEQ. ID. NO: 3). that would appear if the identified protein was CYFRA 21-1, was not detected, which suggests that only the entire CK19 protein was present in the sample. It is known that the intact CK19 is rather insoluble; therefore the fraction containing the hydrophobic proteins was also analyzed with mass spectrometry. In this latter fraction peptides were detected ranging from CK19 amino acid 8 to 398, which demonstrated that the full length CK19 was present in the cell free supernatant (FIG. 2, Table 2). Importantly, the peptide 'GQVG-GQVSVEVDSAPGTDLAK' (amino acid 227-247) (SEQ. ID. NO: 2) was detected and partially sequenced with LC MS/MS (FIG. 2B, SEQ. ID. NO: 15), which can only emerge from the entire CK19 protein.

TABLE 2

CK19 peptides detected with tandem mass spectrometry

| Cell free sample supernatant | CK19 peptides detected with tandem mass spectrometry | |
|---|---|---|
| *Fraction 1[A]* | | |
| MCF-7 | SQYEVMAEQNR (254-264)[C] | SEQ. ID. NO: 4 |
| | DAEAWFTSR (266-274)[C] | SEQ. ID. NO: 5 |
| | SEVTDLRR (294-301)[C] | SEQ. ID. NO: 6 |
| | LEQEIATYR (373-381)[C] | SEQ. ID. NO: 7 |
| C643 | nd[D] | |
| PC3 | nd[D] | |
| culture media | nd[D] | |
| *Fraction 2[B]* | | |
| MCF-7 | QSSATSSFGGLGGGSVR (8-24)[C] | SEQ. ID. NO: 8 |
| | LTMQNLNDR (82-90)[C] | SEQ. ID. NO: 9 |
| | IVLQIDNAR (151-159)[C] | SEQ. ID. NO: 10 |

TABLE 2-continued

CK19 peptides detected with tandem mass spectrometry

| Cell free sample supernatant | CK19 peptides detected with tandem mass spectrometry | |
|---|---|---|
| | GQVGGQVSVEVDSAPGTDLAK (227-247)[C] | SEQ. ID. NO: 2 |
| | SQYEVMAEQNR (254-264)[C] | SEQ. ID. NO: 11 |
| | EVAGHTEQLQMSR (281-293)[C] | SEQ. ID. NO: 12 |
| | LEQEIATYR (373-381)[C] | SEQ. ID. NO: 13 |
| | SLLEGQEDHYNNLSASK (382-398)[C] | SEQ. ID. NO: 14 |
| C643 | nd[D] | |
| PC3 | nd[D] | |
| culture media | nd[D] | |

[A]Fraction 1 contains the soluble proteins
[B]Fraction 2 contains the hydrophobic proteins
[C]Amino acid numbers refer to the full length CK19 sequence
[D]CK19 peptides were not detected with tandem mass spectrometry Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A method of detecting viable disseminated epithelial cells in a sample from a patient, the method comprising:
   isolating a sample from a patient, the sample comprising viable cells;
   culturing the cells in a cell culture media for a time sufficient for an epithelial cell-specific marker to be released from the viable cells into the cell culture media, the released marker comprising a substantially full-length cytokeratin; and
   detecting the released epithelial cell-specific marker comprising the substantially full-length cytokeratin that has been released into the cell culture media;
   wherein detection of the released epithelial cell-specific marker comprising the substantially full-length cytokeratin in the cell culture media indicates the presence of viable disseminated epithelial cells in the sample.

2. The method of claim 1, wherein the sample is isolated from blood, bone marrow or lymph nodes.

3. The method of claim 1, wherein the sample is depleted of CD-45+ cells.

4. The method of claim 1, wherein the released marker comprises a substantially full-length cytokeratin 19.

5. The method of claim 4, wherein the marker comprises a sequence that is at least 90% identical to a full-length polypeptide of SEQ. ID. NO: 1.

6. The method of claim 4, wherein the marker comprises a sequence that is at least 95% identical to a full-length polypeptide of SEQ. ID. NO: 1.

7. The method of claim 1, wherein detecting the released marker comprises binding the released marker with a binding partner.

8. The method of claim 7, wherein the binding partner comprises an antibody.

9. The method of claim 8, wherein the antibody recognizes an epitope on the marker 5' to an enzymatic cleavage site on the marker.

10. The method of claim 1, wherein detecting the released marker comprises using mass spectrometry.

11. The method of claim 10, wherein the released marker detected by mass spectrometry comprises a polypeptide sequence substantially identical to SEQ. ID. NO: 2, SEQ. ID. NO: 8, SEQ. ID. NO:9, SEQ. ID. NO: 10 or SEQ. ID. NO: 15.

12. A method of identifying a substantially full-length epithelial cell marker released from viable cells, the method comprising:
    isolating a sample from a patient, the sample comprising viable cells;
    culturing the cells in a cell culture media for a time sufficient for the epithelial cell marker to be released from the viable cells into the cell culture media, the released marker comprising a substantially full-length polypeptide having an enzymatic cleavage site within the full-length polypeptide, the full-length polypeptide comprising substantially full-length cytokeratin; and
    detecting a portion of the full-length polypeptide comprising the substantially full-length cytokeratin that has been released in the cell culture media, the portion being 5' to the enzymatic cleavage site;
    wherein detection of the 5' portion identifies the full-length epithelial cell marker released from viable cells.

13. The method of claim 12, wherein the 5' portion is detected using an antibody.

14. The method of claim 12, wherein the 5' portion is detected using mass spectrometry.

15. The method of claim 14, wherein the 5' portion comprises a polypeptide sequence substantially identical to SEQ. ID. NO: 2, SEQ. ID. NO: 8, SEQ. ID. NO: 9, SEQ. ID. NO: 10 or SEQ. ID. NO: 15.

16. The method of claim 12 wherein the substantially full-length polypeptide comprises cytokeratin 19.

17. The method of claim 12, wherein identifying the full-length marker in a sample not normally associated with epithelial cells indicates the presence of a disseminated epithelial tumor cell.

18. A method of detecting viable epithelial cells in tissue sample, the method comprising:
    obtaining a tissue sample from a patient, the sample comprising viable cells;
    culturing the cells in a cell culture media for a time sufficient for an epithelial cell-specific marker to be released from the viable cells into the cell culture media, the released marker comprising a substantially full-length cytokeratin;
    detecting the released epithelial cell-specific marker comprising the substantially full-length cytokeratin that has been released into the cell culture media; and
    wherein detection of the released epithelial cell-specific marker comprising the substantially full-length cytokeratin in the cell culture media indicates the presence of a viable epithelial cell in the tissue sample.

19. The method of claim 18, wherein the marker comprises a substantially full-length cytokeratin 19.

20. The method of claim 18, wherein the tissue sample is breast tissue.

* * * * *

UNITED STATES PATENT AND TRADEMARK OFFICE
CERTIFICATE OF CORRECTION

PATENT NO. : 8,524,493 B2
APPLICATION NO. : 12/439744
DATED : September 3, 2013
INVENTOR(S) : Panabières et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1214 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 15

<210> SEQ ID NO 1
<211> LENGTH: 400
<212> TYPE: PRT
<213> ORGANISM: Homo sapiens

<400> SEQUENCE: 1

Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Gly Tyr Gly Gly Gly
    50                  55                  60
```

-continued

Tyr Gly Gly Val Leu Thr Ala Ser Asp Gly Leu Leu Ala Gly Asn Glu
 65                  70                  75                  80

Lys Leu Thr Met Gln Asn Leu Asn Asp Arg Leu Ala Ser Tyr Leu Asp
                 85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
    130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
    210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
        275                 280                 285

Leu Gln Met Ser Arg Ser Glu Val Thr Asp Leu Arg Arg Thr Leu Gln
    290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Ala Asp Val
            340                 345                 350

Arg Ala Asp Ser Glu Arg Gln Asn Gln Glu Tyr Gln Arg Leu Met Asp
        355                 360                 365

Ile Lys Ser Arg Leu Glu Gln Glu Ile Ala Thr Tyr Arg Ser Leu Leu
370                 375                 380

Glu Gly Gln Glu Asp His Tyr Asn Asn Leu Ser Ala Ser Lys Val Leu
385                 390                 395                 400

<210> SEQ ID NO 2
<211> LENGTH: 21
<212> TYPE: PRT
<213> ORGANISM: Homo sapiens

<400> SEQUENCE: 2

Gly Gln Val Gly Gly Gln Val Ser Val Glu Val Asp Ser Ala Pro Gly
1               5                   10                  15

Thr Asp Leu Ala Lys
            20

<210> SEQ ID NO 3

```
<211> LENGTH: 10
<212> TYPE: PRT
<213> ORGANISM: Homo sapiens

<400> SEQUENCE: 3

Asp Ser Ala Pro Gly Thr Asp Leu Ala Lys
1               5                   10

<210> SEQ ID NO 4
<211> LENGTH: 11
<212> TYPE: PRT
<213> ORGANISM: Homo sapiens

<400> SEQUENCE: 4

Ser Gln Tyr Glu Val Met Ala Glu Gln Asn Arg
1               5                   10

<210> SEQ ID NO 5
<211> LENGTH: 9
<212> TYPE: PRT
<213> ORGANISM: Homo sapiens

<400> SEQUENCE: 5

Asp Ala Glu Ala Trp Phe Thr Ser Arg
1               5

<210> SEQ ID NO 6
<211> LENGTH: 8
<212> TYPE: PRT
<213> ORGANISM: Homo sapiens

<400> SEQUENCE: 6

Ser Glu Val Thr Asp Leu Arg Arg
1               5

<210> SEQ ID NO 7
<211> LENGTH: 9
<212> TYPE: PRT
<213> ORGANISM: Homo sapiens

<400> SEQUENCE: 7

Leu Glu Gln Glu Ile Ala Thr Tyr Arg
1               5

<210> SEQ ID NO 8
<211> LENGTH: 17
<212> TYPE: PRT
<213> ORGANISM: Homo sapiens

<400> SEQUENCE: 8

Gln Ser Ser Ala Thr Ser Ser Phe Gly Gly Leu Gly Gly Gly Ser Val
1               5                   10                  15

Arg

<210> SEQ ID NO 9
<211> LENGTH: 9
<212> TYPE: PRT
<213> ORGANISM: Homo sapiens

<400> SEQUENCE: 9

Leu Thr Met Gln Asn Leu Asn Asp Arg
1               5

<210> SEQ ID NO 10
<211> LENGTH: 9
```

```
<212> TYPE: PRT
<213> ORGANISM: Homo sapiens

<400> SEQUENCE: 10

Ile Val Leu Gln Ile Asp Asn Ala Arg
1               5

<210> SEQ ID NO 11
<211> LENGTH: 11
<212> TYPE: PRT
<213> ORGANISM: Homo sapiens

<400> SEQUENCE: 11

Ser Gln Tyr Glu Val Met Ala Glu Gln Asn Arg
1               5                   10

<210> SEQ ID NO 12
<211> LENGTH: 13
<212> TYPE: PRT
<213> ORGANISM: Homo sapiens

<400> SEQUENCE: 12

Glu Val Ala Gly His Thr Glu Gln Leu Gln Met Ser Arg
1               5                   10

<210> SEQ ID NO 13
<211> LENGTH: 9
<212> TYPE: PRT
<213> ORGANISM: Homo sapiens

<400> SEQUENCE: 13

Leu Glu Gln Glu Ile Ala Thr Tyr Arg
1               5

<210> SEQ ID NO 14
<211> LENGTH: 17
<212> TYPE: PRT
<213> ORGANISM: Homo sapiens

<400> SEQUENCE: 14

Ser Leu Leu Glu Gly Gln Glu Asp His Tyr Asn Asn Leu Ser Ala Ser
1               5                   10                  15

Lys

<210> SEQ ID NO 15
<211> LENGTH: 9
<212> TYPE: PRT
<213> ORGANISM: Homo sapiens

<400> SEQUENCE: 15

Gln Val Ser Val Glu Val Asp Ser Ala
1               5
```